(12) United States Patent
Komoriya et al.

(10) Patent No.: US 7,736,835 B2
(45) Date of Patent: *Jun. 15, 2010

(54) FLUORINE-CONTAINING CYCLIC COMPOUND, FLUORINE-CONTAINING POLYMER COMPOUND, RESIST MATERIAL USING SAME AND METHOD FOR FORMING PATTERN

(75) Inventors: Haruhiko Komoriya, Kawagoe (JP); Shinichi Sumida, Kawagoe (JP); Michitaka Ootani, Kawagoe (JP); Takeo Komata, Kawagoe (JP); Kazuhiko Maeda, Chiyoda-ku (JP)

(73) Assignee: Central Glass Company, Limited, Ube-shi (JP)

( * ) Notice: Subject to any disclaimer, the term of this patent is extended or adjusted under 35 U.S.C. 154(b) by 210 days.

This patent is subject to a terminal disclaimer.

(21) Appl. No.: 10/589,807

(22) PCT Filed: Feb. 17, 2005

(86) PCT No.: PCT/JP2005/002400

§ 371 (c)(1),
(2), (4) Date: May 15, 2007

(87) PCT Pub. No.: WO2005/080306

PCT Pub. Date: Sep. 1, 2005

(65) Prior Publication Data

US 2008/0003517 A1    Jan. 3, 2008

(30) Foreign Application Priority Data

Feb. 20, 2004  (JP) .............................. 2004-044142

(51) Int. Cl.
G03F 7/004 (2006.01)
C08F 18/20 (2006.01)
C07C 35/18 (2006.01)

(52) U.S. Cl. ..................... 430/270.1; 568/812; 568/826; 526/245; 430/322

(58) Field of Classification Search .............. 430/270.1, 430/326, 322; 526/245, 247, 242; 560/205, 560/206, 207, 210, 223; 568/812, 826, 841, 568/842, 822

See application file for complete search history.

(56) References Cited

U.S. PATENT DOCUMENTS

| | | | |
|---|---|---|---|
| 3,627,847 A | 12/1971 | Langkammerer | |
| 6,200,725 B1 | 3/2001 | Takechi et al. | |
| 6,329,125 B2 | 12/2001 | Takechi et al. | |
| 7,205,443 B2* | 4/2007 | Komata et al. | 568/842 |
| 7,385,091 B2* | 6/2008 | Komata et al. | 568/826 |
| 7,402,626 B2* | 7/2008 | Maeda et al. | 524/544 |
| 2003/0224283 A1* | 12/2003 | Allen et al. | 430/270.1 |
| 2003/0232940 A1* | 12/2003 | Komoriya et al. | 526/242 |
| 2005/0250898 A1* | 11/2005 | Maeda et al. | 524/544 |
| 2006/0074263 A1* | 4/2006 | Kobayashi et al. | 568/663 |

FOREIGN PATENT DOCUMENTS

| | | |
|---|---|---|
| JP | 8-241913 A | 9/1996 |
| JP | 10-161313 A | 6/1998 |
| JP | 2000-89463 | 3/2000 |
| JP | 2003-238620 A | 8/2003 |
| JP | 2004-4226 A | 1/2004 |
| JP | 2004-4576 A | 1/2004 |
| JP | 2004-46098 A | 2/2004 |

OTHER PUBLICATIONS

Burger, et al., Synthese von 4,4-Bis(trifluormethyl)-1-oxabuta-1,3-dienen, Journal fuer praktische Chemie, Chemiker-Zeitung, vol. 334, 1992, pp. 219-226.
International Search Report dated May 17, 2005 including English Translation of relevant portion (Five (5) pages).
H. Ito, H.D. Troung, et al. "Fluoropolymer Resists: Progress and Properties", Journal of Photopolymer Science and Technology, vol. 16, No. 4, 2003, pp. 523-536.
Francis Houlihan, et al. "New Fluorinated Resins for 157 nm Lithography Application", Journal of Photopolymer Science and Technology, vol. 16, No. 4, (2003), pp. 581-590.
Taiwanese Search Report dated Apr. 3, 2008 (seven (7) pages).
Klaus Burger et al., "Synthese of 4,4-Bis(trifluoromethyl)-1-oxabuta-1,3-dienen", Journal fuer Praktische Chemie Chemike-Zeitung, 1992, vol. 334, pp. 219-226 including English translation of abstract.
Yoshimitsu Suda et al., "Highly Diastereoselective Alcoholysis of σ-Symmetric Dicarboxylic Acid Anhydrides Using 1-Phenyl-3,3-bis(trifluoromethyl)propan-1,3-diol", The Chemical Society of Japan, Chemistry Letters, 1992, pp. 389-392.

\* cited by examiner

*Primary Examiner*—Cynthia H Kelly
*Assistant Examiner*—Anca Eoff
(74) *Attorney, Agent, or Firm*—Crowell & Moring LLP

(57) ABSTRACT

The present invention relates to, for example, a fluorine-containing cyclic compound represented by the following general formula (1).

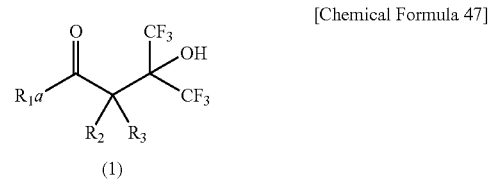

[Chemical Formula 47]

(1)

In the general formula (1), R1a is a $C_1$-$C_{25}$ cyclic alkyl group, cyclic alkenyl group or cyclic alkynyl group; each of R2 and R3 is independently a hydrogen atom, a halogen atom, or a $C_1$-$C_{25}$ straight-chain, branched or cyclic alkyl group; and each of R1a, R2 and R3 may contain fluorine atom, oxygen atom, sulfur atom, nitrogen atom or an atomic group containing a carbon-carbon double bond.

12 Claims, No Drawings

FLUORINE-CONTAINING CYCLIC COMPOUND, FLUORINE-CONTAINING POLYMER COMPOUND, RESIST MATERIAL USING SAME AND METHOD FOR FORMING PATTERN

TECHNICAL FIELD

The present invention relates to a novel fluorine-containing cyclic compound, a fluorine-containing polymer compound, a resist material using the same, and particularly to a chemically-amplified resist material and a pattern forming method, of which researches have recently actively been conducted.

BACKGROUND OF THE INVENTION

In recent years, due to the development of digital equipment such as computer, the operation data to deal with and the throughput of two-dimensional and three-dimensional image data have become enormous. In order to quickly process such information, a large-volume, high-speed memory and a high-performance microprocessor have become necessary. Furthermore, it is expected that a trend to broadband will be accelerated and that the processing capacity required of digital equipment will increase more and more, along with the development of network such as the Internet.

In order to accomplish this demand, many of device equipment, which are represented by semiconductor devices, are required to achieve further densification and integration. In particular, the demand for photolithography technique, which makes a fine processing possible, has become stricter year by year. For producing a DRAM having a degree of integration of 1G bits or greater, it is necessary to have a processing technique of the minimum line width of 0.13 micrometers or less. In response to that, the utilization of a photolithography using ArF excimer laser (193 nm) has started. Furthermore, the development of photolithography using F2 (157 nm) is going on for the purpose of forming fine patterns.

In these wavelength regions, novolac and polyvinyl phenol series resins, which have conventionally been used for resist materials, are too high in light absorption. Therefore, it is not possible to use them. Therefore, acrylic resins (see Patent Publication 1) and cycloolefin resins (see Patent Publication 2) have been examined. However, resins that are highly transparent at a wavelength of F2 (157 nm) are very limited, and therefore advantage of fluororesins has become clear. In particular, there have been reports that fluorine-containing resist resins containing hydroxyl group have a characteristic that is also superior in hydrophilicity, and therefore they are expected very much (Non-patent Publications 1 and 2).

The introduction of fluorine atom improves transparency in ultraviolet region, but at the same time it lowers etching resistance. In connection with polymerizability too, there remained many problems that monomers, in which fluorine atom and trifluoromethyl group are directly bonded to conventional norbornene rings, are low in polymerizability to lead to low yield and are not capable of providing sufficient molecular weights as materials. Therefore, functions that are achievable by these existing compounds are not necessarily sufficient. There has been a desire for a novel monomer or its raw material that is capable of efficiently providing a further superior polymer.

On the other hand, epoxy resin and the like are used in the field of semiconductor device package, but there is used a method in which fine particles of silicon oxide (SiO2) having a thermal expansion coefficient close to that of a device substrate (Si substrate) are added to a sealing resin material for the purpose of reducing thermal stress upon mounting onto a printed wiring board. However, in conventional technique, a plastic package of conventional structure using epoxy resin inferior to metal, ceramics, etc. in thermal conductivity is inferior in radiation characteristic and is quite high in thermal resistance. Therefore, it was disadvantageous in terms of a long-term reliability as an IC of high electric-power consumption such as power IC or as a package of IC operating at high speed. Furthermore, fine particles of $SiO_2$ added to resin to make it have low stress are very hard. Therefore, thermal stress generated upon mounting onto printed wiring board has added a large pressure locally to the device surface, thereby generating device destruction. In other words, there has been a demand for a material that is high in heat resistance and hardly adds thermal stress to the device surface in the field of semiconductor package (see Patent Publication 3). In fact, it is difficult to satisfy the demanded performances by a single semiconductor package material. Thus, various protecting films, etc. are used together. We can say that the package material and the protecting film are integrated and achieve their functions by compensating their respective weaknesses. A passivation film is used for preventing the intrusion of water and impurities into semiconductor chip, and a buffer coating film is used for loosening stress concentration occurring in a package material. Hitherto, inorganic compounds such as silicon oxide have primarily been used for thin film materials, such as insulating film and protecting film, used for semiconductors. Nowadays, however, the usefulness of heat resistant polymer materials such as polyimide have been recognized, and they are used for layer insulation film, passivation film, buffer coating film, etc. For the request of integration and high-speed of semiconductors in recent years, there is a demand for a material corresponding to the high-speed transmission of signals. In high-speed transmission, the propagation delay of signals becomes problematic, but it is effective to make a material have a lower dielectric constant since the propagation delay is proportional to relative dielectric constant of a material. Nowadays, it is known that fluororesins are low in dielectric constant, and fluorine-containing polyimide is also investigated as one of potential materials. A resin, into which fluorine atom has been introduced, has special properties possessed by fluorine, such as water repellency, non-adhesiveness, etc., and sometimes it can be utilized for the aimed use. Sometimes, however, its utilization was difficult due to its specificity. Along with the appearance of new semiconductor applied products in recent years, semiconductor packages have also been diversified. There have been various demands for them to be more compact, thinner, lower in dielectric constant, etc. A package material satisfying these has been demanded.

Patent Publication 1: Japanese Patent Laid-open Publication 10-161313

Patent Publication 2: Japanese Patent Laid-open Publication 2000-89463

Patent Publication 3: Japanese Patent Laid-open Publication 8-241913

Non-patent Publication 1: H. Ito, H. D. Truong, et al, J. Photopolym. Sci. Technol., 16, 523-536 (2003)

Non-patent Publication 2: Francis Houlihan, Andrew Romano, Ralph R, Dammel, et al, J. Photopolym. Sci. Technol., 16, 581-590 (2003)

SUMMARY OF THE INVENTION

It is an object of the present invention to provide novel fluorine-containing cyclic compound and fluorine-containing polymer compound and to provide a resist material that has a high transparency in a wide wavelength region from ultraviolet region to near-infrared region and has a high adhesion to substrate, film-forming property and high etching resistance, and a pattern-forming method using the same. It is another object of the present invention to provide a package material for semiconductor device.

As a result of a repeated eager examination to solve the above-mentioned task, the present inventors have found a novel fluorine-containing cyclic compound having a cyclic structure such as norbornene ring and a hexafluoroisopropanol structure and have found that a fluorine-containing polymer compound obtained by a polymerization or copolymerization using this compound or a polymerizable monomer derived from this compound has high transparency in a wide wavelength region, high adhesion to substrate, and film-forming property. Furthermore, we have found that this fluorine-containing polymer compound has a high etching resistance derived from the cyclic structure and is effective as a resist material. Furthermore, we have found a pattern-forming method using this fluorine-containing polymer compound. On the other hand, we have found that this fluorine-containing polymer compound is high in heat resistance due to having a cyclic structure in the molecule, is superior in applicability due to a good solvent solubility derived from hexafluoroisopropanol structure, and is superior in film-forming property and formability, thereby completing the present invention. Furthermore, in case that a semiconductor device is formed into a package by using this fluorine-containing polymer compound itself or by adding hardener to this, we have found that stress to the device substrate is very small and high credibility can be obtained.

DETAILED DESCRIPTION

The present invention provides novel fluorine-containing cyclic compound and fluorine-containing polymer compound and provides a resist material that has a high transparency in a wide wavelength region from ultraviolet region to near-infrared region and has a high adhesion to substrate, film-forming property and high etching resistance, and a pattern-forming method using the same. The fluorine-containing polymer compound is suitable as a package material for semiconductor device.

In the following, the present invention is described in detail. The fluorine-containing cyclic compound represented by the general formula (1) or (2) of the present invention is a novel fluorine-containing cyclic compound having a cyclic structure such as norbornene ring and a hexafluoroisopropanol structure. In general, it is known that, as the fluorine content is increased, the improvement of transparency in a wide wavelength region from ultraviolet region to near-infrared region and the lowering of refractive index are induced. On the other hand, as the fluorine content is increased, lowering of adhesion to substrate and lowering of film-forming property are also induced. Therefore, it was difficult to achieve them together with high transparency and low refractive index. However, due to that a compound represented by the general formula (1) or (2) has a hexafluoroisopropanol structure, a polymer compound derived from this became possible to have high adhesion to substrate and high film-forming property.

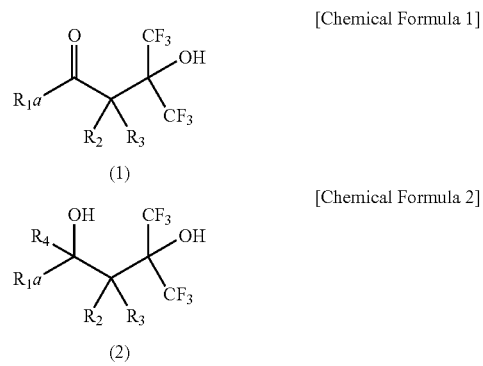

In a fluorine-containing cyclic compound represented by the general formula (1) or (2) according to the present invention, R1a is a $C_1$-$C_{25}$ cyclic alkyl group, cyclic alkenyl group or cyclic alkynyl group. A cyclic skeleton is preferable, since it contributes to etching resistance that is necessary for resist material. A polycyclic skeleton is more preferably used, since it significantly contributes to etching resistance. By introducing a cyclic structure into the molecule, it becomes possible to increase glass transition temperature (Tg) of a polymer compound derived from this. By adjusting the proportion of the cyclic structure contained in the polymer compound, it becomes also possible to adjust Tg. Tg is an important element for the acid diffusion rate of a chemically amplified positive-type resist. It is an important element for reducing or adjusting thermal expansion coefficient in the field of package material for semiconductor device and buffer coating.

On the other hand, in conventional fluorine-containing cyclic compounds, none of them was applied to resist materials and semiconductor package materials by leading it into polymer compounds.

R2 and R3 are not particularly limited as long as they do not substantially damage the properties of this compound. Each of them is independently a hydrogen atom, a halogen atom, or a $C_1$-$C_{25}$ straight-chain, branched or cyclic alkyl group. R1-R3 may contain fluorine atom, oxygen atom, sulfur atom, nitrogen atom or an atomic group containing a carbon-carbon double bond.

A fluorine-containing cyclic compound represented by the general formula (3) according to the present invention is a polymerizable monomer that can be derived from the compound according to the above general formula (1) or (2). The advantageous effect by containing fluorine atom, the advantageous effect by having a hexafluoroisopropanol structure, and the advantageous effect by having a cyclic structure, particularly a polycyclic skeleton, are the same as those shown in connection with the above general formula (1) or (2). That is, in the general formula (3), R1b is a $C_1$-$C_{25}$ cyclic alkyl group, cyclic alkenyl group, cyclic alkynyl group, aryl group, or heterocyclic group, and may contain fluorine atom, oxygen atom, sulfur atom, nitrogen atom or an atomic group containing a carbon-carbon double bond. R2 to R7 are not particularly limited as long as they do not substantially damage the properties of this compound. Each of them is independently a hydrogen atom, a halogen atom, or a $C_1$-$C_{25}$ straight-chain, branched or cyclic alkyl group, and may contain fluorine atom, oxygen atom, sulfur atom, nitrogen atom or an atomic group containing a carbon-carbon double bond. R8 is a carbonyl group or methylene group, or a single bond.

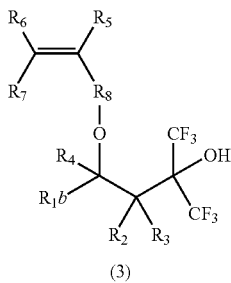

(3)

[Chemical Formula 3]

A fluorine-containing cyclic compound represented by the general formula (4) or (5) according to the present invention is a polymerizable monomer that can be derived from the compound according to the above general formula (1) or (2). The advantageous effect by containing fluorine atom, the advantageous effect by having a hexafluoroisopropanol structure, and the advantageous effect by having a cyclic structure, particularly a polycyclic skeleton, are the same as those shown in connection with the above general formula (1) or (2). That is, in the general formula (4) or (5), R2, R3, R4 and R9 to R15 are not particularly limited as long as they do not substantially damage the properties of this compound. Each of them is independently a hydrogen atom, a halogen atom, or a $C_1$-$C_{25}$ straight-chain, branched or cyclic alkyl group, and may contain fluorine atom, oxygen atom, sulfur atom, or nitrogen atom. R10 and R11 or R12 and R13 may be bonded together to form a ring. In such case, it is an $C_1$-$C_{25}$ alkylene group that may contain a hetero atom such as oxygen, sulfur and nitrogen. "a" is 0 or 1, "b" is an integer of 0-2, and "c" is an integer of 0-2.

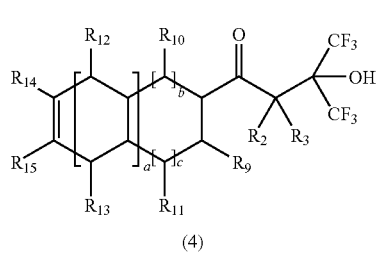

(4)

[Chemical Formula 4]

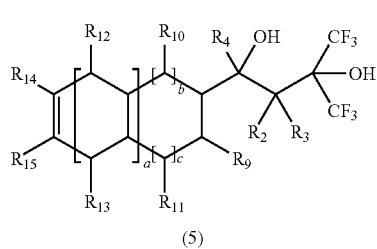

(5)

[Chemical Formula 5]

A fluorine-containing cyclic compound represented by the general formula (6) according to the present invention is a polymerizable monomer that can be derived from the compound according to the above general formula (4) or (5). The advantageous effect by containing fluorine atom, the advantageous effect by having a hexafluoroisopropanol structure, and the advantageous effect by having a cyclic structure, particularly a polycyclic skeleton, are the same as those shown in connection with the above general formula (1) or (2). That is, in the general formula (6), R2 to R7 and R9 to R15 are not particularly limited as long as they do not substantially damage the properties of this compound. Each of them is independently a hydrogen atom, a halogen atom, or a $C_1$-$C_{25}$ straight-chain, branched or cyclic alkyl group, and may contain fluorine atom, oxygen atom, sulfur atom, or nitrogen atom. R8 is a carbonyl group or methylene group or a single bond. R10 and R11, R12 and R13, or R14 and R15 may be bonded together to form a ring. In such case, it is an $C_1$-$C_{25}$ alkylene group that may contain a hetero atom such as oxygen, sulfur and nitrogen. "a" is 0 or 1, "b" is an integer of 0-2, and "c" is an integer of 0-2.

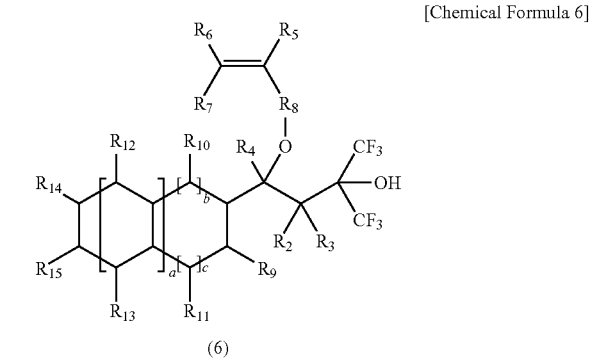

(6)

[Chemical Formula 6]

In a fluorine-containing cyclic compound represented by the general formula (7) or (8) according to the present invention, the advantageous effect by containing fluorine atom, the advantageous effect by having a hexafluoroisopropanol structure, and the advantageous effect by having a cyclic structure, particularly a polycyclic skeleton, are the same as those shown in connection with the above general formula (1) or (2). That is, R2, R3 and R4 are not particularly limited as long as they do not substantially damage the properties of this compound. Each of them is independently a hydrogen atom, a halogen atom, or a $C_1$-$C_{25}$ straight-chain, branched or cyclic alkyl group, and may contain fluorine atom, oxygen atom, sulfur atom, or nitrogen atom.

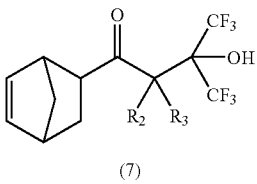

(7)

[Chemical Formula 7]

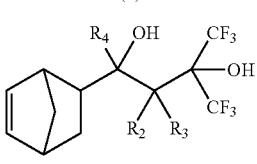

(8)

[Chemical Formula 8]

A fluorine-containing cyclic compound represented by the general formula (9) according to the present invention is a polymerizable monomer that can be derived from the compound according to the above general formula (7) or (8). The advantageous effect by containing fluorine atom, the advantageous effect by having a hexafluoroisopropanol structure, and the advantageous effect by having a cyclic structure, particularly a polycyclic skeleton, are the same as those shown in connection with the above general formula (1) or (2). That is, in the general formula (9), R2 to R7 are not particularly limited as long as they do not substantially damage the properties of this compound. Each of them is independently a hydrogen atom, a halogen atom, or a $C_1$-$C_{25}$ straight-chain, branched or cyclic alkyl group, and may contain fluorine atom, oxygen atom, sulfur atom, or nitrogen atom. R8 is a carbonyl group or methylene group or a single bond.

[Chemical Formula 9]

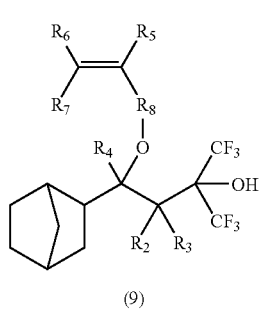

(9)

A fluorine-containing polymer compound represented by the general formula (10) according to the present invention is a polymer compound obtained by polymerization in a manner to contain a polymerizable monomer according to the general formula (3). The advantageous effect by containing fluorine atom, the advantageous effect by having a hexafluoroisopropanol structure, and the advantageous effect by having a cyclic structure, particularly a polycyclic skeleton, are the same as those shown in connection with the above general formula (1) or (2). That is, it is a fluorine-containing polymer compound having a weight average molecular weight of 1,000 to 1,000,000, which is characterized in that it contains a repeating unit represented by the general formula (10). R1b and R2 to R8 are not particularly limited, as long as they do not substantially damage the properties of this compound, and are the same as those shown in the general formula (3).

[Chemical Formula 10]

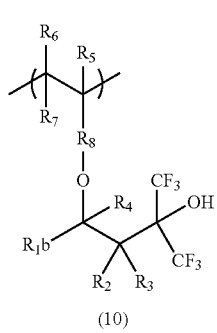

(10)

A fluorine-containing polymer compound represented by the general formula (11) according to the present invention is a polymer compound obtained by polymerization in a manner to contain a polymerizable monomer according to the general formula (6). The advantageous effect by containing fluorine atom, the advantageous effect by having a hexafluoroisopropanol structure, and the advantageous effect by having a cyclic structure, particularly a polycyclic skeleton, are the same as those shown in connection with the above general formula (1) or (2). That is, it is a fluorine-containing polymer compound having a weight average molecular weight of 1,000 to 1,000,000, which is characterized in that it contains a repeating unit represented by the general formula (11). If the molecular weight is less than this, it is not sufficient in terms of mechanical strength and film-forming property. If the molecular weight is greater than this, it is not preferable in terms of solubility in solvent and film-forming property. R2 to R15 are not particularly limited, as long as they do not substantially damage the properties of this compound, and are the same as those shown in the general formula (6).

[Chemical Formula 11]

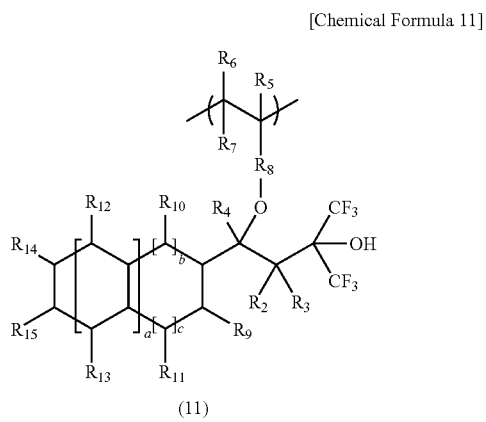

(11)

A fluorine-containing polymer compound represented by the general formula (12) according to the present invention is a polymer compound obtained by polymerization in a manner to contain a polymerizable monomer according to the general formula (9). The advantageous effect by containing fluorine atom, the advantageous effect by having a hexafluoroisopropanol structure, and the advantageous effect by having a cyclic structure, particularly a polycyclic skeleton, are the same as those shown in connection with the above general formula (1) or (2). That is, it is a fluorine-containing polymer compound having a weight average molecular weight of 1,000 to 1,000,000, which is characterized in that it contains a repeating unit represented by the general formula (12). If the molecular weight is less than this, it is not sufficient in terms of mechanical strength and film-forming property. If the molecular weight is greater than this, it is not preferable in terms of solubility in solvent and film-forming property. R2 to R8 are not particularly limited, as long as they do not substantially damage the properties of this compound, and are the same as those shown in the general formula (9).

[Chemical Formula 12]

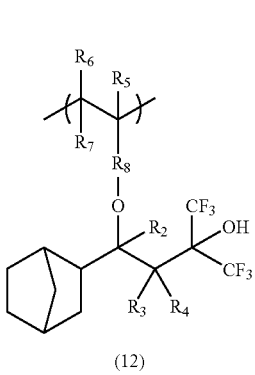

(12)

A fluorine-containing polymer compound represented by the general formula (13) or (14) according to the present invention is a polymer compound obtained by polymerization in a manner to contain a polymerizable monomer according to the general formula (4) or (5). The advantageous effect by containing fluorine atom, the advantageous effect by having a hexafluoroisopropanol structure, and the advantageous effect by having a cyclic structure, particularly a polycyclic skeleton, are the same as those shown in connection with the above general formula (1) or (2). That is, it is a fluorine-containing polymer compound having a weight average molecular weight of 1,000 to 1,000,000, which is characterized in that it contains a repeating unit represented by the general formula (13) or (14). If the molecular weight is less than this, it is not sufficient in terms of mechanical strength and film-forming property. If the molecular weight is greater than this, it is not preferable in terms of solubility in solvent and film-forming property. R2, R3, R4 and R9 to R15 are not particularly limited, as long as they do not substantially damage the properties of this compound, and are the same as those shown in the general formula (4) or (5).

[Chemical Formula 13]

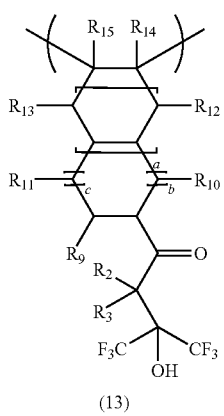

(13)

[Chemical Formula 14]

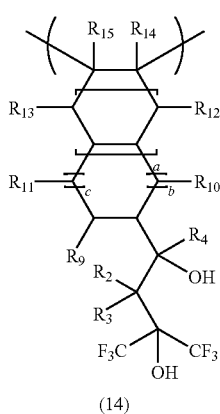

(14)

A fluorine-containing polymer compound represented by the general formula (15) or (16) according to the present invention is a polymer compound obtained by polymerization in a manner to contain a polymerizable monomer according to the general formula (7) or (8). The advantageous effect by containing fluorine atom, the advantageous effect by having a hexafluoroisopropanol structure, and the advantageous effect by having a cyclic structure, particularly a polycyclic skeleton, are the same as those shown in connection with the above general formula (1) or (2). That is, it is a fluorine-containing polymer compound having a weight average molecular weight of 1,000 to 1,000,000, which is characterized in that it contains a repeating unit represented by the general formula (15) or (16). If the molecular weight is less than this, it is not sufficient in terms of mechanical strength and film-forming property. If the molecular weight is greater than this, it is not preferable in terms of solubility in solvent and film-forming property. R2, R3, and R4 are not particularly limited, as long as they do not substantially damage the properties of this compound, and are the same as those shown in the general formula (7) or (8).

[Chemical Formula 15]

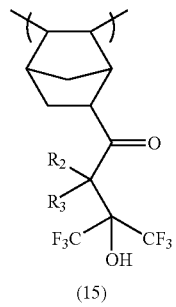

(15)

[Chemical Formula 16]

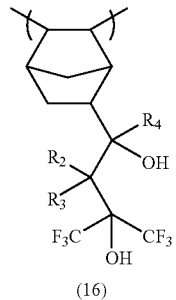

(16)

A fluorine-containing polymer compound, which is characterized in that it contains a repeating unit represented by the general formula (17) according to the present invention, is a polymer compound obtained by polymerization in a manner to contain a polymerizable monomer according to the general formulas (13) to (16) and an α-trifluoromethylacrylic ester. A copolymer of the cyclic olefin and the α-trifluoromethylacrylic ester becomes a material that is superior in heat resistance and high in mechanical strength and Tg, since it contains a cyclic structure in the main chain. It is also possible to adjust it to have necessary properties by changing the selection and the composition of the monomers to be combined in the copolymerization reaction. The advantageous effect by containing fluorine atom, the advantageous effect by having a hexafluoroisopropanol structure, and the advantageous effect by having a cyclic structure, particularly a polycyclic skeleton, are the same as those shown in connection with the above general formula (1) or (2). That is, it is a fluorine-containing polymer compound having a weight average molecular weight of 1,000 to 1,000,000, which is characterized in that it contains a repeating unit represented by the general formula (17). If the molecular weight is less than this, it is not sufficient in terms of mechanical strength and film-forming property. If the molecular weight is greater than this, it is not preferable in terms of solubility in solvent and film-forming property. It is a hydrogen atom, or a $C_1$-$C_{25}$ straight-chain, branched or cyclic alkyl group, and may contain fluorine atom, oxygen atom, sulfur atom, nitrogen atom, hydroxyl group or hexafluorocarbinol group.

[Chemical Formula 17]

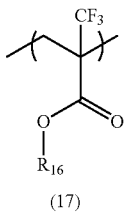

(17)

A polymer compound according to the present invention, which is characterized in that it contains a repeating unit having an acid-labile group is a polymer compound obtained by polymerization in a manner to contain a polymerizable monomer having an acid-labile group, or one obtained by replacing a part of a polymer compound with an acid-labile group. As examples of the acid-labile group, they can be used without particular limitation, as long as they are groups that generates elimination by the effect of photoacid generator, hydrolysis, etc. As specific examples are cited, it is possible to cite alkoxycarbonyl group, acetal group, silyl group, acyl group, etc. The alkoxycarbonyl group can be exemplified by tert-butoxycarbonyl group, tert-amyloxycarbonyl group, methoxycarbonyl group, ethoxycarbonyl group, i-propoxycarbonyl group and the like. As the acetal group, it is possible to cite methoxymethyl group, ethoxyethyl group, butoxyethyl group, cyclohexyloxyethyl group, benzyloxyethyl group, phenethyloxyethyl group, ethoxypropyl group, benzyloxypropyl group, phenethyloxypropyl group, ethoxybutyl group, ethoxyisobutyl group, etc. It is also possible to use an acetal group in which a vinyl ether has been added to the hydroxy group. As the silyl group, it is possible to cite, for example, trimethylsilyl group, ethyldimethylsilyl group, methyldiethylsilyl group, triethylsilyl group, i-propyldimethylsilyl group, methyldi-i-propylsilyl group, tri-i-propylsilyl group, t-butyldimethylsilyl group, methyldi-t-butylsilyl group, tri-t-butylsilyl group, phenyldimethylsilyl group, methyldiphenylsilyl group, triphenylsilyl group, and the like. As the acyl group, it is possible to cite acetyl group, propionyl group, butyryl group, heptanoyl group, hexanoyl group, valeryl group, pivaloyl group, isovaleryl group, lauryloyl group, myristoyl group, palmitoyl group, stearoyl group, oxalyl group, malonyl group, succinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydratoropoyl group, atoropoyl group, cinnamoyl group, furoyl group, thenoyl group, nicotinoyl group, isonicotinoyl group, and the like. Furthermore, it is also possible to use ones in which fluorine atoms have been substituted for a part or entirety of hydrogen atoms of these acid labile groups.

The purpose of using an acid labile group is to achieve positive photosensitivity and dissolution in an alkali aqueous solution after exposure to a high energy radiation such as a far infrared radiation of a wavelength of 300 nm or shorter, excimer laser, X ray or the like, or electron beam. One having fluorine atom at its functional group is for providing transparency, and one having a cyclic structure is for providing characteristics such as etching resistance and high glass transition point. They can be used differently depending on the applied fields of the present invention.

In the fluorine-containing cyclic compound and the fluorine-containing polymer compound of the present invention, it is possible to protect a part or the entirety of the hydroxyl groups, which are contained in the molecule, with a protecting group. It is possible to change and adjust polarity of the molecule by changing the type of the protecting group or the degree of protection. With this, it is possible to make solubility in solvent, applicability to substrate, surface tension, dispersibility of photoacid generator, acid diffusion rate, etc. appropriate. The protecting group is a $C_1$-$C_{25}$ straight-chain, branched or cyclic hydrocarbon group or aromatic hydrocarbon group. It can be exemplified by methyl group, ethyl group, propyl group, isopropyl group, cyclopropyl group, n-propyl group, iso-propyl group, sec-butyl group, tert-butyl group, n-pentyl group, cyclopentyl group, sec-pentyl group, neopentyl group, hexyl group, cyclohexyl group, ethylhexyl group, norbornel group, adamantyl group, vinyl group, allyl group, butenyl group, pentenyl group, ethynyl group, phenyl group, benzyl group, 4-methoxybenzyl group and the like. They may be ones in which a part or the entirety of the above functional groups has been replaced with fluorine atoms. As those containing oxygen atom, it is possible to cite alkoxycarbonyl group, acetal group, acyl group and the like. The alkoxycarbonyl group can be exemplified by tert-butoxycarbonyl group, tert-amyloxycarbonyl group, methoxycarbonyl group, ethoxycarbonyl group, i-propoxycarbonyl group and the like. As the acetal group, there are cited acyclic ethers, such as methoxymethyl group, methoxyethoxymethyl group, ethoxyethyl group, butoxyethyl group, cyclohexyloxyethyl group, benzyloxyethyl group, phenethyloxyethyl group, ethoxypropyl group, benzyloxypropyl group, phenethyloxypropyl group, ethoxybutyl group and ethoxyisobutyl group, and cyclic ethers, such as tetrahydrofuranyl group and tetrahydropyranyl group. As the acyl group, it is possible to cite acetyl group, propionyl group, butyryl group, heptanoyl group, hexanoyl group, valeryl group, pivaloyl group, isovaleryl group, lauryloyl group, myristoyl group, palmitoyl group, stearoyl group, oxalyl group, malonyl group, succinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydratoropoyl group, atoropoyl group, cinnamoyl group, furoyl group, thenoyl group, nicotinoyl group, isonicotinoyl group, and the like. Furthermore, it is also possible to use ones in which fluorine atoms have been substituted for a part or entirety of hydrogen atoms of the above substituents.

It is also possible to introduce an acid-labile protecting group into the hydroxyl group. It is preferably used as a method for adjusting solubility before and after the exposure in the case of the use for resist. In particular, hexafluoroisopropanol group is an acid hydroxyl group and functions as a soluble group to an alkali developing solution. In other words, it is possible to make it function as a positive-type resist that makes alkali development possible by protecting the hexafluoroisopropanol group in the molecule with an acid-labile protecting group, followed by mixing with a photoacid generator to produce a resist and then exposing this.

The fluorine-containing cyclic compound and the fluorine-containing polymer compound of the present invention are effective in a resist material of any type such as positive type, negative type and chemically amplified type. In each use, it can be used by changing its mixing amount and mixing method.

A fluorine-containing polymer compound of the present invention is one prepared by homopolymerization of a fluorine-containing cyclic compound represented by the general formulas (1) to (9) or by copolymerization with another in a manner to contain it. They are those represented by the general formulas (10) to (17), a fluorine-containing polymer compound of any of the general formulas (10) to (17), which is characterized in that it contains a repeating unit having an acid-labile group, and a fluorine-containing polymer compound of any of the general formulas (10) to (17), which is characterized in that the hydroxyl groups contained in the molecule are partially or entirely protected with protecting groups.

As a monomer that can be copolymerized with the fluorine-containing cyclic compound of the present invention is specifically exemplified, it is preferable to conduct a copolymerization with at least one monomer selected from at least maleic anhydride, acrylic esters, fluorine-containing acrylic esters, methacrylic esters, fluorine-containing methacrylic esters, styrene compounds, fluorine-containing styrene compounds, vinyl ethers, fluorine-containing vinyl ethers, allyl ethers, fluorine-containing allyl ethers, olefins, fluorine-containing olefins, norbornene compounds, fluorine-containing norbornene compounds, sulfur dioxide, and vinyl silane.

The polymerization method of a polymer compound according to the present invention is not particularly limited, as long as it is a generally used method. Radical polymerization, ionic polymerization and the like are preferable. In some cases, it is possible to use coordinated anionic polymerization, living anionic polymerization, cationic polymerization, ring-opening metathesis polymerization, vinylene polymerization, vinyl addition and the like.

The radical polymerization may be conducted by a known polymerization method, such as bulk polymerization, solution polymerization, suspension polymerization or emulsion polymerization, in the presence of a radical polymerization initiator or radical initiating source, with a batch-wise, half-continuous or continuous operation.

The radical polymerization initiator is not particularly limited. As its examples, azo compounds, peroxide compounds and redox compounds are cited. In particular, azobisbutyronitrile, t-butylperoxypivalate, di-t-butylperoxide, i-butyrylperoxide, lauroylperoxide, succinic acid peroxide, dicinnamylperoxide, di-n-propylperoxydicarbonate, t-butylperoxyallyl monocarbonate, benzoyl peroxide, hydrogen peroxide, ammonium persulfate, and like are preferable.

The reaction vessel used in the polymerization reaction is not particularly limited. Furthermore, a polymerization solvent may be used in the polymerization reaction. As the polymerization solvent, one that does not interfere with the radical polymerization is preferable. Representative ones are ester solvents such as ethyl acetate and n-butyl acetate; ketone solvents such as acetone and methyl isobutyl ketone; hydrocarbon solvents such as toluene and cyclohexane; and alcohol solvents such as methanol, isopropyl alcohol and ethylene glycol monomethyl ether. Furthermore, it is also possible to use solvents such as water, ethers, cyclic ethers, fluorohydrocarbons, and aromatics. These solvents can be used singly or in combination of at least two types. Furthermore, it may be accompanied in use with a molecular weight adjusting agent such as mercaptan. The reaction temperature of the copolymerization reaction is suitably changed depending on the radical polymerization initiator or radical polymerization initiating source. In general, 20-200° C. is preferable. In particular, 30-140° C. is preferable.

On the other hand, the ring-opening metathesis polymerization can be conducted by a known method using a transition metal catalyst in the presence of a cocatalyst.

The polymerization catalyst is not particularly limited. As the examples, Ti, V, Mo and W catalysts are cited. In particular, titanium chloride, vanadium chloride, vanadium trisacetylacetonato, vanadium bisacetylacetonatodichloride, molybdenum chloride, and tungsten chloride and the like are preferable. The amount of the catalyst is from 10 mol % to 0.001 mol %, preferably 1 mol % to 0.01 mol %, relative to the used monomer.

As the cocatalyst, alkylaluminum, alkyltin and the like are cited. In particular, it can be exemplified by aluminum-based ones such as trialkylaluminums such as trimethylaluminum, triethylaluminum, tripropylaluminum, triisopropylaluminum, triisobutylaluminum, tri-2-methylbutylaluminum, tri-3-methylbutylaluminum, tri-2-methylpentylaluminum, tri-3-methylpentylaluminum, tri-4-methylpentylaluminum, tri-2-methylhexylaluminum, tri-3-methylhexylaluminum, and trioctylaluminum; dialkylaluminum halides dimethylaluminum chloride, diethylaluminum chloride, diisopropylaluminum chloride, and diisobutylaluminumchloride; monoalkylaluminum halides such as methylaluminum dichloride, ethylaluminum dichloride, ethylaluminum diiodide, propylaluminum dichloride, isopropylaluminum dichloride, butylaluminum dichloride, and isobutylaluminum dichloride; and alkylaluminum sesquichlorides such as methylaluminum sesquichloride, ethylaluminum sesquichloride, propylaluminum sesquichloride; and isobutylaluminum sesquichloride; tetra-n-butyltin, tetraphenyltin, and triphenylchlorotin. The amount of the cocatalyst is by molar ratio 100 equivalents or less, preferably 30 equivalents or less, relative to the transition metal catalyst.

The polymerization solvent will do, as long as it does not interfere with the polymerization. As its representative ones, it can be exemplified by aromatic hydrocarbons such as benzene, toluene, xylene, chlorobenzene and dichlorobenzene; hydrocarbons such as hexane, heptane and cyclohexane; and halogenated hydrocarbons such as carbon tetrachloride, chloroform, methylene chloride and 1,2-dichloroethane. These solvents may be used alone or in a mixture of at leas two kinds. The reaction temperature is generally preferably −70° C. to 200° C., particularly preferably −30° C. to 60° C.

The vinylene polymerization can be conducted by a known process in the presence of a cocatalyst using a transition metal catalyst, such as iron, nickel, rhodium, palladium and platinum, or a metal catalyst, such as zirconium, titanium, vanadium, chromium, molybdenum, and tungsten.

The polymerization catalyst is not particularly limited. As examples, particularly, there are preferable transition metal compounds such as iron(II) chloride, iron(III) chloride, iron (II) bromide, iron(III) bromide, iron(II) acetate, iron(III) acetylacetate, ferrocene, nickelocene, nickel(II) acetate, nickel bromide, nickel chloride, dichlorohexylnickel acetate, nickel lactate, nickel oxide, nickel tetrafluoroborate, bis(allyl)nickel, bis(cyclopentadienyl)nickel, nickel(II) hexafluoroacetylacetonatotetrahydrate, nickel(II) trifluoroacetylacetonatodihydrate, nickel(II) acetylacetonatotetrahydrate, rhodium(III) chloride, rhodium tris(triphenylphosphine) trichloride, palladium(II) bis(trifluoroacetate), palladium(II) bis(acetylacetonato), palladium(II) 2-ethylhexanoate, palladium(II) bromide, palladium(II) chloride, palladium(II) iodide, palladium(II) oxide, monoacetonitriletris(triphenylphosphine)palladium(II) tretrafluoroborate, tetrakis(acetonitrile)palladium(II) tetrafluoroborate, dichlorobis(acetonitrile)palladium(II), dichlorobis(triphenylphosphine)palladium(II), dichlorobis(benzonitrile)palladium(II), palladium acetylacetonato, palladium bis(acetonitrile) dichloride, palladium bis(dimethylsulfoxide)dichloride and platinum bis(triethylphosphine)hydrobromide, and transition metal compounds such as vanadium(IV) chloride, vanadium trisacetylacetonato, vanadium bisacetylacetonatodichloride, trimethoxy(pentamethylcyclopentadienyl)titanium(IV), bis(cyclopentadienyl)titanium dichloride, and bis(cyclopentadienyl)zirconium dichloride. The catalyst amount is from 10 mol % to 0.001 mol %, preferably from 1 mol % to 0.01 mol %, relative to the used monomer.

As the cocatalyst, alkylaluminoxane, alkylaluminum and the like are cited. In particular, it can be exemplified by methylaluminoxane (MAO), trialkylaluminums such as trimethylaluminum, triethylaluminum, tripropylaluminum, triisopropylaluminum, triisobutylaluminum, tri-2-methylbutylaluminum, tri-3-methylbutylaluminum, tri-2-methylpentylaluminum, tri-3-methylpentylaluminum, tri-4-methylpentylaluminum, tri-2-methylhexylaluminum, tri-3-methylhexylaluminum, and trioctylaluminum; dialkylaluminum halides such as dimethylaluminum chloride, diethylaluminum chloride, diisopropylaluminum chloride, and diisobutylaluminum chloride; monoalkylaluminum halides such as methylaluminum dichloride, ethylaluminum dichloride, ethylaluminum diiodide, propylaluminum dichloride, isopropylaluminum dichloride, butylaluminum dichloride, and isobutylaluminum dichloride; and alkylaluminum sesquichlorides such as methylaluminum sesquichloride, ethylaluminum sesquichloride, propylaluminum sesquichloride, and isobutylaluminum sesquichloride. The amount of the cocatalyst is 50 to 500 equivalents in terms of Al conversion in the case of methylaluminoxane. In the case of other alkylaluminums, it is 100 equivalents or less, preferably 30 equivalents or less, relative to the transition metal catalyst by molar ratio.

The polymerization solvent will do as long as it does not interfere with the polymerization. As representative ones, it can be exemplified by aromatic hydrocarbons such as benzene, toluene, xylene, chlorobenzene, and dichlorobenzene; hydrocarbons such as hexane, heptane, and cyclohexane; halogenated hydrocarbons such as carbon tetrachloride, chloroform, methylene chloride, and 1,2-dichloroethane; dimethylformamide, N-methylpyrrolidone, and N-cyclohexylpyrolidone. These solvents may be used alone or in a mixture of at least two kinds. The reaction temperature is generally preferably −70° C. to 200° C., particularly preferably −40° C. to 80° C.

As a process of removing an organic solvent or water from the obtained solution or dispersion of the polymer compound according to the present invention, a process such as reprecipitation, filtration or heated distillation under reduced pressure is possible.

As a process of forming a fluorine-containing polymer compound according to the present invention into a thin film, for example, it is possible to use a process in which it is dissolved in an organic solvent, followed by application and drying. The organic solvent to be used is not particularly limited, as long as the polymer compound is soluble. It is possible to use ketones such as acetone, methyl ethyl ketone, cyclohexanone, methyl isoamyl ketone and 2-heptanone; polyhydric alcohols such as ethylene glycol, ethylene glycol monoacetate, diethylene glycol, diethylene glycol monoacetate, propylene glycol, propylene glycol monoacetate, dipropylene glycol, or monomethyl ether, monoethyl ether, monopropyl ether, monobutyl ether or monophenyl ether of dipropylene glycol monoacetate, and their derivatives; cyclic ethers such as dioxane; esters such as methyl lactate, ethyl lactate, methyl acetate, ethyl acetate, butyl acetate, methyl pyruvate, ethyl pyruvate, methyl methoxypropionate, and ethyl ethoxypropionate; aromatic solvents such as xylene and toluene; fluorine-series solvents such as fleon, alternative fleon, perfluoro compounds, and hexafluoroisopropyl alcohol; and terpene-based petroleum naphtha solvents and paraffinic solvents, which are high-boiling-point, weak solvents, for the purpose of increasing applicability. These may be used singly or in a mixture of at least two kinds.

A resist composition according to the present invention is one containing a dissolution inhibitor, of which solubility in alkali aqueous solution changes by the action of acid, and the polymer compound or one in which a dissolution inhibitor is built in the polymer compound. These are particularly suitable as positive-type resist materials. They are also suitable as positive-type resists for 248 nm KrF or 193 nm ArF excimer laser or vacuum ultraviolet (typically 157 nm) region $F_2$ laser, electron beam resists, and resists for X-ray, which correspond to a recent trend for finer semiconductors. In other words, the dissolution inhibitor, of which solubility in alkali aqueous solution changes by the action of acid, is such that at least one of hexafluorocarbinol groups becomes an acid-labile group. It can be used without a particular limitation in its structure. General acid-labile groups are the above-mentioned acid-labile groups, and they are functional groups that are severed by acids. The polymer compound using such dissolution inhibitor is insoluble or scarcely soluble in alkali aqueous solution prior to the activating energy ray irradiation. It is hydrolyzed by an acid generated from a photoacid generator by the activating energy ray irradiation and thereby shows solubility in alkali aqueous solution.

The photoacid generator used in the resist material of the present invention is not particularly limited, and an arbitrary one can be selected from those used as acid generators of chemically amplified resists and then used. As examples of such photoacid generators, there are cited bissulfonyldiazomethanes, nitrobenzyl derivatives, onium salts, halogen-containing triazine compounds, cyano group-containing oximesulfonate compounds, and other oximesulfonate compounds. These photoacid generators may be used singly or in a combination of at least two kinds. Its content is generally selected in a range of 0.5 to 20 parts by weight relative to 100 parts by weight of the polymer compound. If this amount is less than 0.5 parts by weight, image formation capability is insufficient. If it exceeds 20 parts by weight, it is difficult to form a homogeneous solution. With this, storage stability tends to be lowered.

A conventional resist pattern forming method can be used as a method for using the resist material of the present invention. That is, firstly a solution of the resist material is applied to a substrate such as silicon wafer with a spinner, followed by drying to form a photosensitive layer. This is exposed to a high-energy ray by an exposure apparatus or the like through a desired mask pattern, followed by heating. Then, this is subjected to a development treatment using a developing solution, for example, an alkali aqueous solution such as 0.1-10 wt % tetramethylammonium hydroxide aqueous solution. This forming method makes it possible to obtain a pattern conforming to the mask pattern. Furthermore, according to need, it is possible to contain additives that are miscible with the resist material, for example, various additives such as additional resins, quencher, plasticizer, stabilizer, coloring agent, surfactant, tackifier, leveling agent, deforming agent, compatibility enhancing agent, adhesion enhancing agent, and antioxidant.

A high-energy ray used in the present invention is not particularly limited. In particular, in the case of conducting a fine processing, it is effective to use an exposure device equipped with a short-wavelength high-energy ray (e.g., $F_2$ excimer laser, ArF excimer laser, KrF excimer laser, or soft X-ray) generating source. It is effective to use an immersion exposure device that makes it possible to conduct a more efficient fine processing in numerical aperture and effective wavelength by using a medium (e.g., water and fluorine-containing solvents), into which the used high-energy ray has a less absorption, at a part of the optical path. The present resist material is also preferable in the case of use in this device.

Fluorine-containing polymer compounds represented by the general formulas (10) to (17), fluorine-containing polymer compounds represented by the general formulas (10) to (17), which are characterized in containing a repeating unit having an acid-labile group, and fluorine-containing polymer compounds represented by the general formulas (10) to (17), which are characterized in that a part or entirety of the hydroxyl groups contained in the molecule is protected with a protecting group, can preferably be used as semiconductor device package materials. Sealing material and overcoat material are representative as semiconductor device package materials. Buffer coat film, passivation film and their protecting film are representative as overcoat materials. The fluorine-containing polymer compound of the present invention is high in heat resistance due to having a cyclic structure in the molecule, is superior in applicability due to a good solvent solubility derived from hexafluoroisopropanol structure, and is superior in film-forming property and formability. It is possible to obtain characteristics suitable to each use by the type of the substituent contained in the molecule, the type of the monomer to be copolymerized, its composition, the compounding ratio to another material to be mixed with, the type of the hardener, etc.

In the fluorine-containing polymer compound according to the present invention, a preferable molecular weight as a semiconductor device package material is in a range of Mw 1,000-1,000,000, preferably Mw 10,000-500,000. If the molecular weight is excessively small, sealing material and protecting film become low in mechanical strength, resulting in growing tendency to generate defects. If the molecular weight is excessively large, solvent solubility becomes low, and film-forming property and formability become low, thereby not sufficiently achieving the original capabilities of the material. For a semiconductor device package material, Tg of at least 100° C. is necessary, preferably 150° C. or higher, more preferably 200° C. or higher. To make it have a higher Tg, it is effective to subject a fluorine-containing polymer compound of the present invention together with hardener to heat treatment or light irradiation to form a cross-linked structure. As the hardener, there are cited organic peroxide, isocyanate, melamine, epoxy compound, polyamine, acid anhydride, and polyhydric phenol. It is preferable to use a combination with curing catalyst, curing assistant, reactive diluent, cross-linking agent or chain extension agent. Curing method is not particularly limited. It is possible to use a known method such as heat, light or radioactive ray. For example, in the case of conducting a sealing of semiconductor, it is preferable to use a curing by heat rather than light from the viewpoint of light transparency. It is possible and preferable to use a blend with filler or another resin for the purpose of improving chemical, mechanical or electrical characteristics. As a method for packaging a semiconductor device, it is possible to use a known method, and it is not particularly limited. For example, there are cited sealing by transfer molding method, sealing by potting method, and thin film forming methods such as spin coating, roll coating and dipping.

In the following, embodiments of the present invention are specifically described by examples, but the present invention is not limited to these examples.

Example 1

Synthesis of Compound 2

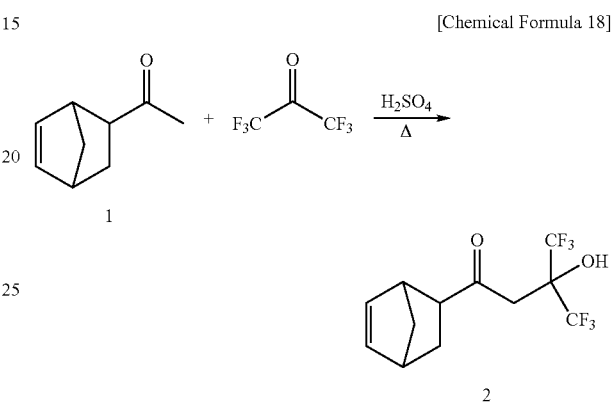

[Chemical Formula 18]

A 50 ml autoclave made of SUS was charged with 2-acetyl-5-norbornene 1 (37.0 g) and concentrated sulfuric acid (0.17 g), followed by sealing. Hexafluoroacetone (65.0 g) was weighed and put into this, followed by heating in an oil bath of 60° C. and stirring for 23 hr. After the reaction, the autoclave was cooled down, followed by adding saturated sodium bicarbonate aqueous solution to the contents and then extraction by adding toluene. The organic phase was washed with saturated brine, followed by concentration and then vacuum distillation, thereby obtaining 23.4 g of a colorless, transparent liquid. This was analyzed by infrared absorption spectrum (IR), nuclear magnetic resonance spectrum (NMR) and a gas chromatograph mass spectrometer (GC-MS). As a result, it was a mixture of two isomers (Isomer 1 and Isomer 2) of the compound 2. An isomer ratio of Isomer 1 to Isomer 2 was 75:25.

Property Data

Compound 2

IR (cm-1): (a mixture of Isomers 1 and 2): 3294, 3069, 2979, 2947, 2877, 1697, 1448, 1273, 1240, 1198, 1164, 1149, 1099, 1033, 979, 709, 636

$^1$H-NMR (TMS, CDCl3): (Isomer 1): 1.36 (m, 1H), 1.52 (m, 2H), 1.83 (m, 1H), 2.94 (q, 2H), 2.97 (brs, 1H), 3.14 (m, 1H), 3.28 (brs, 1H), 5.84 (dd, 1H), 6.22 (dd, 1H), 6.99 (s, 1H), (Isomer 2): 1.31 (m, 1H), 1.52 (m, 2H), 1.95 (m, 1H), 2.97 (brs, 1H), 3.00 (brs, 1H), 3.06 (brs, 1H), 3.14 (m, 1H), 6.14 (dd, 1H), 6.22 (dd, 1H), 7.05 (s, 1H)

$^{19}$F-NMR (CFCl3, CDCl3): (Isomer 1): −78.82 (q, 3H), −78.63 (q, 3H), (Isomer 2): −78.82 (q, 3H), −78.63 (q, 3H)

GC-MS (EI): (Isomer 1): m/e 302 (M+), 237, 217, (Isomer 2): m/e 302 (M+), 237, 217

Example 2

Synthesis of Compound 3

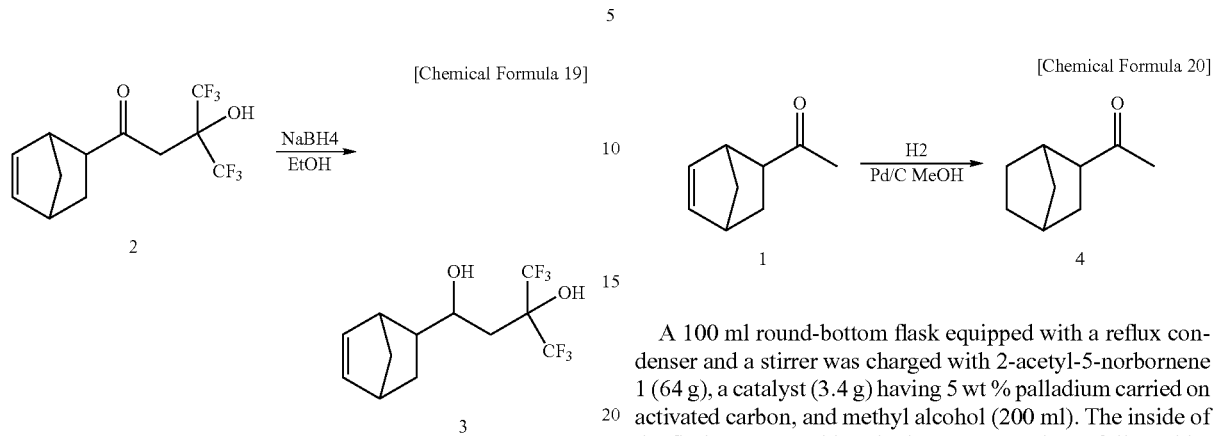

A 100 ml round-bottom flask equipped with a reflux condenser and a stirrer was charged with the compound 2 (5.2 g) and ethyl alcohol (25 ml), followed by adding NaBH4 (0.3 g) with stirring at room temperature and then stirring at room temperature for 30 min. After the reaction, the contents were added to diluted hydrochloric acid (100 ml), followed by adding diisopropyl ether (200 ml) to this to conduct extraction. It was separated into two layers, and the organic layer was taken, followed by washing with saturated sodium bicarbonate aqueous solution and saturated brine. The obtained solution was concentrated, followed by recrystallization with n-heptane, thereby obtaining white-color crystals (2.2 g). This was analyzed by infrared absorption spectrum (IR), nuclear magnetic resonance spectrum (NMR) and a gas chromatograph mass spectrometer (GC-MS). As a result, it was a mixture of four isomers (Isomers 1-4) of the compound 3. An isomer ratio of Isomer 1:Isomer 2:Isomer 3:Isomer 4 was 64:19:11:6.

Property Data

Compound 3

IR (cm-1): (a mixture of Isomers 1, 2, 3 and 4): 3425, 3068, 2979, 2933, 2908, 2868, 1314, 1281, 1225, 1202, 1166, 1151, 1140, 1052, 1042, 1004, 979, 719

$^1$H-NMR (TMS, CDCl3): (Isomer 1): 0.52 (m, 1H), 1.28-1.53 (m, 2H), 1.83-2.39 (m, 5H), 2.60-2.99 (m, 2H), 3.61 (t, 1H), 6.01 (dd, 1H), 6.22 (s, 1H), 6.27 (dd, 1H), (Isomer 2): 0.93 (m, 1H), 1.28-1.53 (m, 2H), 1.83-2.39 (m, 5H), 2.60-2.99 (m, 2H), 3.71 (t, 1H), 5.91 (dd, 1H), 6.13 (s, 1H), 6.27 (dd, 1H), (Isomer 3): 0.52 (m, 1H), 1.28-1.53 (m, 2H), 1.83-2.39 (m, 5H), 2.60-2.99 (m, 2H), 4.05 (t, 1H), 6.11 (dd, 1H), 6.27 (s, 1H), 6.27 (dd, 1H), (Isomer 4): 1.03 (m, 1H), 1.28-1.53 (m, 2H), 1.83-2.39 (m, 5H), 2.60-2.99 (m, 2H), 3.95 (t, 1H), 6.27 (s, 1H), 6.27 (m, 2H)

$^{19}$F-NMR (CFCl3, CDCl3): (a mixture of Isomers 1, 2, 3 and 4): −80.01 (q, 3H), −76.08 (q, 3H)

GC-MS (EI): (Isomer 1): m/e 304 (M+), 286 (—H2O), 267 (—H2O, —F), 237, (Isomer 2): m/e 304 (M+), 286 (—H2O), 267 (—H2O, —F), 237, (Isomer 3): m/e 304 (M+), 286 (—H2O), 267 (—H2O, —F), 237, (Isomer 4): m/e 304 (M+), 286 (—H2O), 267 (—H2O, —F), 237

Example 3

Synthesis of Compound 4

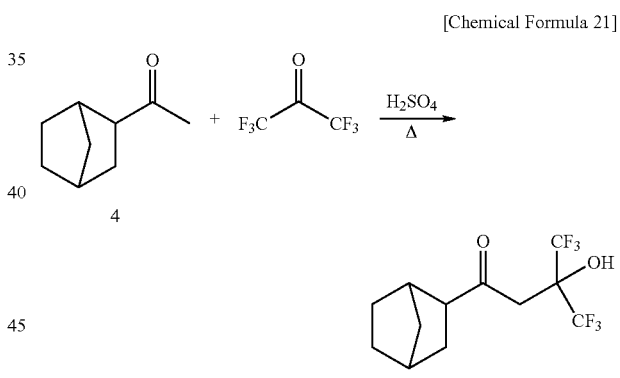

A 100 ml round-bottom flask equipped with a reflux condenser and a stirrer was charged with 2-acetyl-5-norbornene 1 (64 g), a catalyst (3.4 g) having 5 wt % palladium carried on activated carbon, and methyl alcohol (200 ml). The inside of the flask was turned into hydrogen atmosphere, followed by stirring at room temperature for 14 hours. After the reaction, the contents were filtered by Celite, and the filtrate was subjected to vacuum distillation, thereby obtaining the compound 4 (53.3 g).

Example 4

Synthesis of Compound 5

A 50 ml autoclave made of SUS was charged with the compound 4 (50.0 g) and concentrated sulfuric acid (0.41 g), followed by sealing. Hexafluoroacetone (73.0 g) was weighed and put into this, followed by heating in an oil bath of 60° C. and stirring for 41 hr. After the reaction, the autoclave was cooled down, followed by adding the contents to saturated sodium bicarbonate aqueous solution and then extraction by adding diisopropyl ether (200 ml). It was separated into two layers, and the organic layer was taken, followed by washing with saturated brine. The obtained solution was concentrated, followed by vacuum distillation, thereby obtaining a colorless, transparent liquid (92.4 g). This was analyzed by infrared absorption spectrum (IR), nuclear magnetic resonance spectrum (NMR) and a gas chromatograph mass spectrometer (GC-MS). As a result, it was a mixture of two isomers (Isomer 1 and Isomer 2) of the compound 5. An isomer ratio of Isomer 1 to Isomer 2 was 70:30.

Property Data

Compound 5

IR (cm-1): (a mixture of Isomers 1 and 2): 3301, 2960, 2877, 1696, 1455, 1367, 1322, 1273, 1238, 1194, 1163, 1027, 977, 719, 697, 651

$^1$H-NMR (CDCl3): (Isomer 1): 1.10-1.70 (m, 7H), 1.91 (m, 1H), 2.35 (t, 1H), 2.50 (m, 2H), 2.91 (d, 1H), 3.01 (d, 1H), 7.07 (s, 1H), (Isomer 2): 1.10-1.70 (m, 7H), 1.73 (m, 1H), 2.32 (t, 1H), 2.65 (t, 1H), 2.81 (d, 1H), 2.95 (m, 1H), 3.01 (d, 1H), 7.06 (s, 1H)

$^{19}$F-NMR (CFCl3, CDCl3): (Isomer 1): −78.82 (q, 3H), −78.65 (q, 3H), (Isomer 2): −79.07 (q, 3H), −78.49 (q, 3H)

GC-MS (EI): (Isomer 1): m/e 304 (M+), 286 (—H2O), 263, 237, (Isomer 2): m/e 304 (M+), 286 (—H2O), 263, 237

Example 5

Synthesis of Compound 6

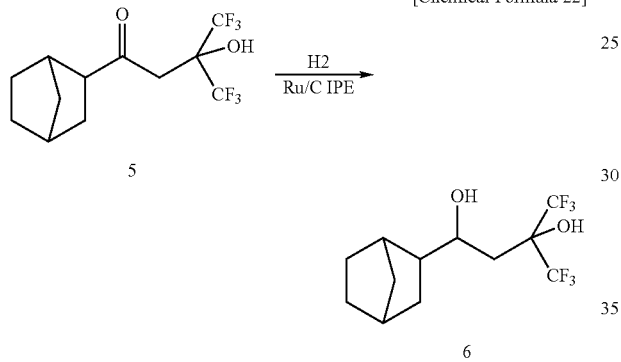

[Chemical Formula 22]

A 1,000 ml autoclave made of SUS was charged with the compound 5 (91.0 g), a catalyst (9.1 g) having 5 wt % ruthenium carried on activated carbon, and diisopropyl ether (300 ml), followed by sealing. The inside of the autoclave was depressurized, followed by heating in an oil bath of 100° C. Then, hydrogen was introduced into the autoclave. Stirring was continued for 14 hours, while adjusting the amount of hydrogen introduced in a manner that the pressure inside of the autoclave is always set to 0.7-1.0 MPa. After the reaction, the contents were filtered by Celite, and the filtrate was concentrated. This was recrystallized by n-heptane, thereby obtaining white-color crystals (82.7 g). This was analyzed by infrared absorption spectrum (IR), nuclear magnetic resonance spectrum (NMR) and a gas chromatograph mass spectrometer (GC-MS). As a result, it was a mixture of four isomers (Isomers 1-4) of the compound 6. An isomer ratio of Isomer 1:Isomer 2:Isomer 3:Isomer 4 was 37:36:17:10.

Property Data

Compound 6

IR (cm-1): (a mixture of Isomers 1, 2, 3 and 4): 3448, 3093, 2958, 2915, 2867, 1457, 1281, 1227, 1204, 1162, 1152, 1138, 1051, 1019, 994, 930, 850, 716, 671

$^1$H-NMR (CDCl$_3$): (Isomer 1): 0.90-2.42 (m, 14H), 3.89 (t, 1H), 6.33 (s, 1H), (Isomer 2): 0.90-2.42 (m, 14H), 3.75 (t, 1H), 6.33 (s, 1H), (Isomer 3): 0.90-2.42 (m, 14H), 4.00 (t, 1H), 6.29 (s, 1H), (Isomer 4): 0.90-2.42 (m, 14H), 4.03 (t, 1H), 6.44 (s, 1H)

$^{19}$F-NMR (CFCl3, CDCl$_3$): (Isomer 1): −79.98 (q, 3H), −76.08 (q, 3H), (Isomer 2): −80.00 (q, 3H), −75.99 (q, 3H), (Isomer 3): −80.00 (q, 3H), −76.02 (q, 3H), (Isomer 4): −79.93 (q, 3H), −75.99 (q, 3H)

GC-MS (EI): (Isomer 1): m/e 306 (M+), 288 (—H2O), 260, 237), (Isomer 2): m/e 306 (M+), 288 (—H2O), 260, 237, (Isomer 3): m/e 306 (M+), 305, 288 (—H2O), 260, 237, (Isomer 4): m/e 306 (M+), 304, 288 (—H2O), 259, 246

Example 6

Synthesis of Compound 7

[Chemical Formula 23]

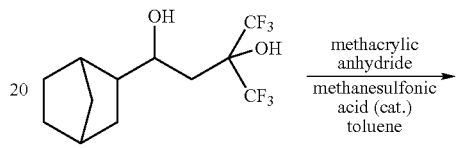

A 1,000 ml round-bottom flask equipped with a reflux condenser and a stirrer was charged with the compound 6 (64.9 g), methacrylic anhydride (36.0 g), methanesulfonic acid (5.3 g), and toluene (325 ml). This was heated in an oil bath of 90° C., and stirring was conducted for 3 hours. After the reaction, the reaction solution was added to saturated sodium bicarbonate aqueous solution, followed by adding 500 ml of toluene to conduct extraction. It was separated into two layers, and the organic layer was taken, followed by washing with saturated brine and then adding phenothiazine (0.33 g). The obtained solution was concentrated, followed by vacuum distillation, thereby obtaining 63.2 g of a colorless, transparent liquid. This was analyzed by infrared absorption spectrum (IR), nuclear magnetic resonance spectrum (NMR) and a gas chromatograph mass spectrometer (GC-MS). As a result, it was a mixture of four isomers of the compound 7. An isomer ratio of Isomer 1:Isomer 2:Isomer 3:Isomer 4 was 38:34:17:11

Property Data

Compound 7

IR (cm-1): (a mixture of Isomers 1, 2, 3 and 4): 3301, 2955, 2874, 1688, 2634, 1455, 1203, 1171, 1143, 1050, 1022, 1009, 946, 815, 715, 660

$^1$H-NMR (CDCl3): (Isomer 1): 0.75-1.55 (m, 8H), 1.75 (m, 1H), 1.95 (t, 3H), 2.09-2.45 (m, 4H), 4.91 (m, 1H), 5.67 (m, 1H), 6.18 (m, 1H), 6.21 (s, 1H), (Isomer 2): 0.75-1.55 (m, 8H), 1.75 (m, 1H), 1.97 (t, 3H), 2.09-2.45 (m, 4H), 4.82 (m, 1H), 5.57 (s, 1H), 5.67 (m, 1H), 6.18 (m, 1H), (Isomer 3): 0.75-1.55 (m, 8H), 1.75 (m, 1H), 1.96 (t, 3H), 2.09-2.45 (m, 4H), 4.98 (m, 1H), 5.67 (m, 1H), 6.05 (s, 1H), 6.18 (m, 1H), (Isomer 4): 0.75-1.55 (m, 8H), 1.75 (m, 1H), 1.96 (t, 3H), 2.09-2.45 (m, 4H), 5.11 (m, 1H), 5.67 (m, 1H), 5.80 (s, 1H), 6.18 (m, 1H)

$^{19}$F-NMR (CFCl3, CDCl$_3$): (Isomer 1): −79.29 (q, 3H), −77.00 (q, 3H), (Isomer 2): −79.09 (q, 3H), −77.14 (q, 3H), (Isomer 3): −79.00 (q, 3H), −77.34 (q, 3H), (Isomer 4): −79.09 (q, 3H), −77.65 (q, 3H)

GC-MS (EI): (Isomer 1): m/e 374 (M+), 359, 314, 305 (—CF3), 288, (Isomer 2): m/e 374 (M+), 359, 333, 316, 305 (—CF3), (Isomer 3): m/e 374 (M+), 356 (—H2O), 305 (—CF3), 288, (Isomer 4): m/e 374 (M+), 356 (—H2O), 305 (—CF3), 288

Example 7

Synthesis of Polymer Compound 8

[Chemical Formula 24]

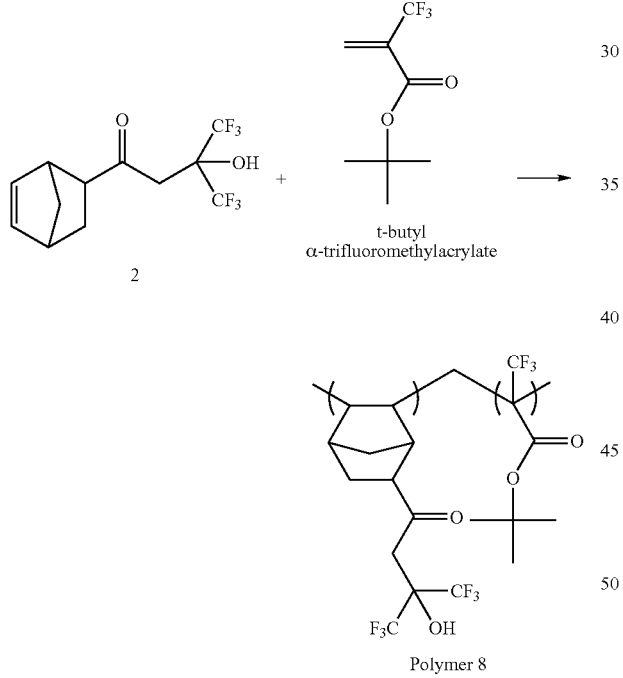

Polymer 8

A 100 ml round-bottom flask equipped with a reflux condenser and a stirrer was charged with the compound 2 (12.1 g), t-butyl α-trifluoromethylacrylate (7.9 g), azobisisobutyronitrile (AIBN) (0.44 g), and n-butyl acetate (11.0 ml), followed by replacing the inside of the flask with nitrogen. This was heated in an oil bath of 60° C., and stirring was conducted for 18 hours. After the reaction, it was added to n-hexane (600 ml), followed by stirring. The resulting precipitate was taken out. This was dried at 55° C. for 18 hours, thereby obtaining the polymer compound 8 (9.6 g) of a white-color solid. The molecular weight was determined from GPC (standard polystyrene). The results are shown in Table 1.

Example 8

Synthesis of Polymer Compound 9

[Chemical Formula 25]

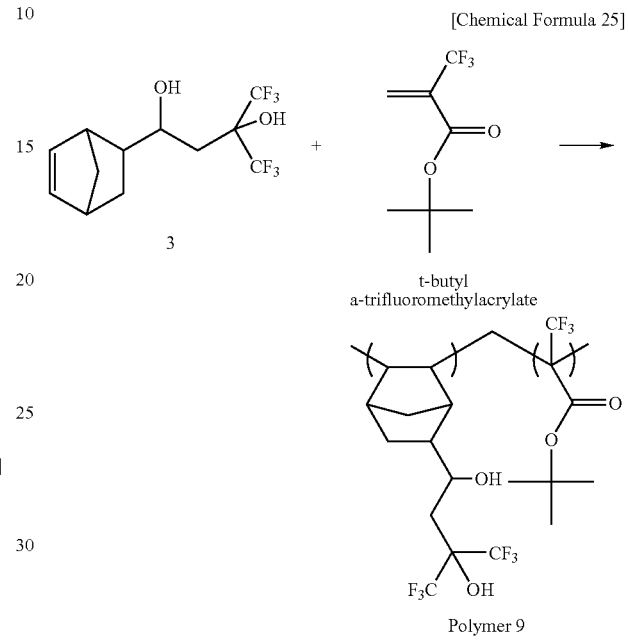

Polymer 9

A 50 ml round-bottom flask equipped with a reflux condenser and a stirrer was charged with the compound 3 (1.5 g), t-butyl α-trifluoromethylacrylate (1.0 g), AIBN (0.20 g), and n-butyl acetate (1.0 ml), followed by replacing the inside of the flask with nitrogen. This was heated in an oil bath of 60° C., and stirring was conducted for 18 hours. After the reaction, it was added to n-hexane (120 ml), followed by stirring. The resulting precipitate was taken out. This was dried at 55° C. for 18 hours, thereby obtaining the polymer compound 9 (1.3 g) of a white-color solid. The molecular weight was determined from GPC (standard polystyrene). The results are shown in Table 1.

Example 9

Synthesis of Polymer Compound 10

[Chemical Formula 26]

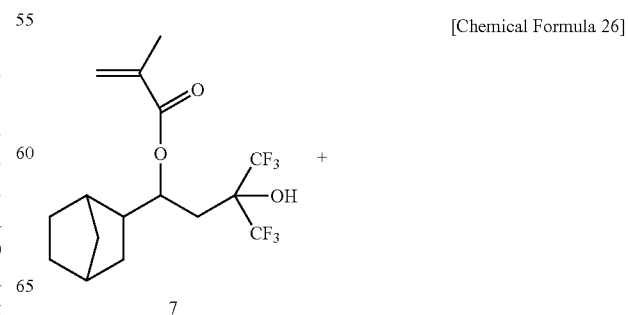

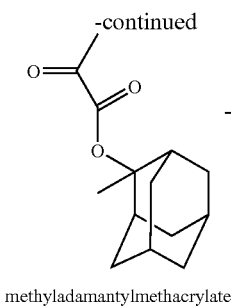

methyladamantylmethacrylate

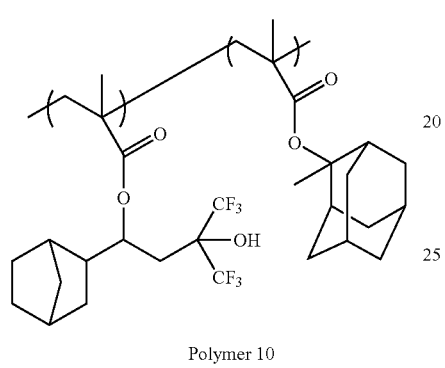

Polymer 10

A 300 ml round-bottom flask equipped with a reflux condenser and a stirrer was charged with the compound 7 (10.0 g), methyladamantylmethacrylate (6.3 g), AIBN (0.35 g), methyl ethyl ketone (82 ml) and n-dodecylmercaptane (0.22 g), followed by replacing the inside of the flask with nitrogen. This was heated in an oil bath of 70° C., and stirring was conducted for 18 hours. After the reaction, it was added to n-hexane (600 ml), followed by stirring. The resulting precipitate was taken out. This was dried at 55° C. for 18 hours, thereby obtaining the polymer compound 10 (11.7 g) of a white-color solid. The molecular weight was determined from GPC (standard polystyrene). The results are shown in Table 1.

Example 10

Synthesis of Polymer Compounds 11 and 12

[Chemical Formula 27]

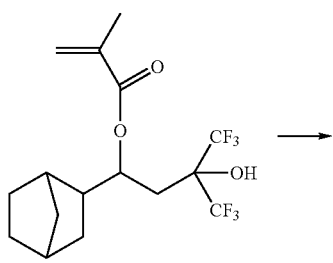

7

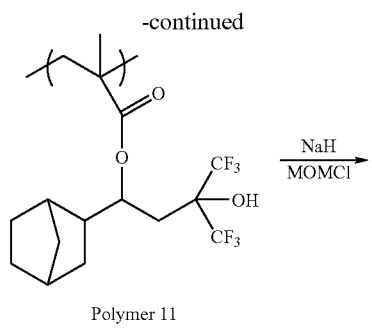

Polymer 11

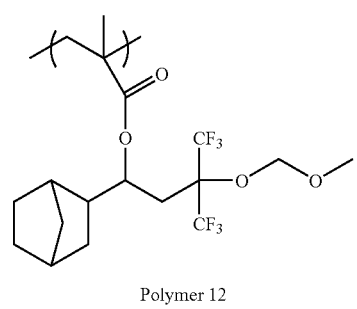

Polymer 12

A 300 ml round-bottom flask equipped with a reflux condenser and a stirrer was charged with the compound 7 (10.0 g), AIBN (0.18 g), methyl ethyl ketone (50 ml) and n-dodecylmercaptane (0.11 g), followed by replacing the inside of the flask with nitrogen. This was heated in an oil bath of 70° C., and stirring was conducted for 18 hours. After the reaction, it was added to n-hexane (430 ml), followed by stirring. The resulting precipitate was taken out. This was dried at 55° C. for 18 hours, thereby obtaining the polymer compound 11 (8.7 g) of a white-color solid. The molecular weight was determined from GPC (standard polystyrene). The results are shown in Table 1.

Then, a 100 ml round-bottom flask equipped with a reflux condenser and a stirrer was charged with the polymer compound 11 (2.0 g) and dehydrated tetrahydrofuran (30 ml) to dissolve it. The inside of the flask was turned into nitrogen atmosphere, followed by cooling with ice, adding NaH (0.16 g) and stirring for 30 min. Furthermore, stirring was conducted at room temperature for 1 hr, followed by adding chloromethyl methyl ether (MOMCl) (0.43 g) and stirring at room temperature for 1 hr. After the reaction, the solution was added to a mixed solvent of water and methanol (1:1 by volume, 200 ml). The resulting precipitate was well washed with water. The obtained white-color solid was dissolved in acetone (10 ml), followed by filtration. The filtrate was added to n-hexane (200 ml), followed by stirring. The resulting precipitate was taken out. This was dried at 55° C. for 18 hours, thereby obtaining the polymer compound 12 (1.6 g) of a white-color solid. The molecular weight was determined from GPC (standard polystyrene). The results are shown in Table 1.

Example 11

Synthesis of Polymer Compound 13

[Chemical Formula 28]

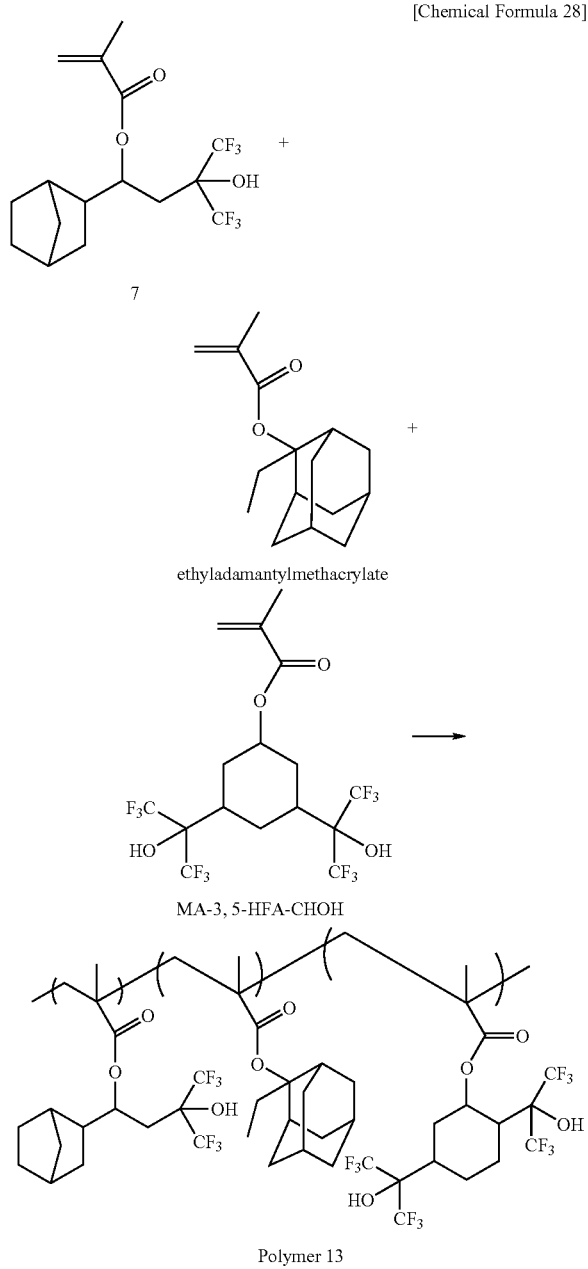

Polymer 13

A 500 ml round-bottom flask equipped with a reflux condenser and a stirrer was charged with the compound 7 (10.0 g), ethyladamantylmethacrylate (6.4 g), MA-3,5-HFA-CHOH (3.6 g), AIBN (0.53 g), methyl ethyl ketone (148 ml) and n-dodecylmercaptane (0.33 g), followed by replacing the inside of the flask with nitrogen. This was heated in an oil bath of 70° C., and stirring was conducted for 18 hours. After the reaction, it was added to n-hexane (900 ml), followed by stirring. The resulting precipitate was taken out. This was dried at 55° C. for 18 hours, thereby obtaining the polymer compound 13 (17.2 g) of a white-color solid. The molecular weight was determined from GPC (standard polystyrene). The results are shown in Table 1.

Example 12

Synthesis of Polymer Compound 14

[Chemical Formula 29]

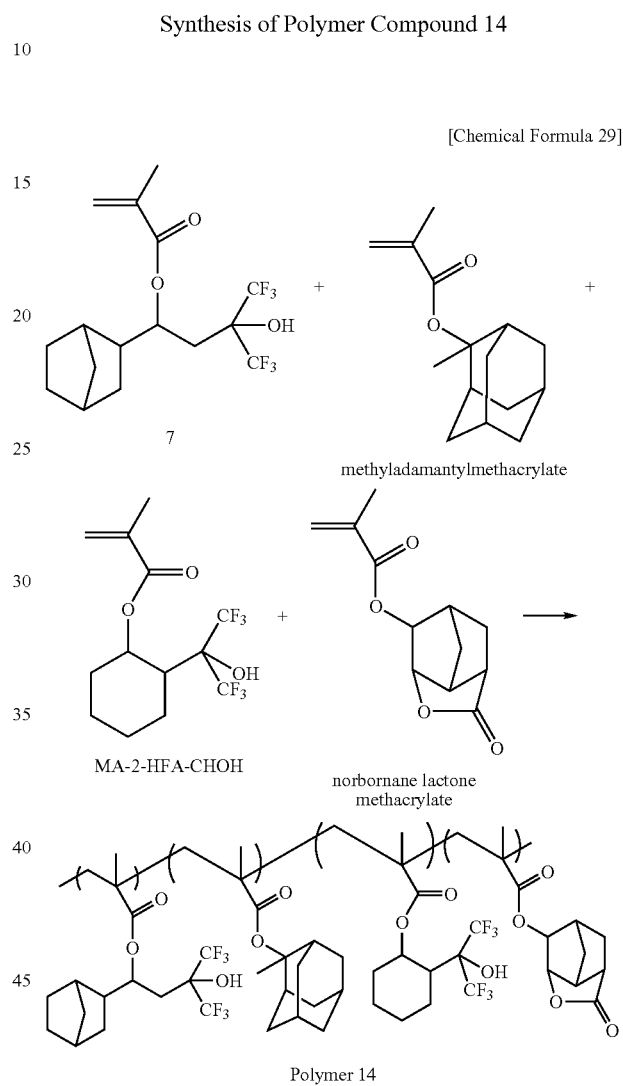

Polymer 14

A 500 ml round-bottom flask equipped with a reflux condenser and a stirrer was charged with the compound 7 (7.8 g), methyladamantylmethacrylate (4.9 g), MA-2-HFA-CHOH (4.7 g), norbornane lactone methacrylate (3.1 g), AIBN (0.51 g), methyl ethyl ketone (128 ml) and n-dodecylmercaptane (0.30 g), followed by replacing the inside of the flask with nitrogen. This was heated in an oil bath of 70° C., and stirring was conducted for 18 hours. After the reaction, it was added to n-hexane (800 ml), followed by stirring. The resulting precipitate was taken out. This was dried at 55° C. for 18 hours, thereby obtaining the polymer compound 14 (16.6 g) of a white-color solid. The molecular weight was determined from GPC (standard polystyrene). The results are shown in Table 1.

TABLE 1

| Ex. | Charged Monomers, etc. | Formed Polymer | Yield | Molecular Weight Mw (Mw/Mn) |
|---|---|---|---|---|
| 7 | Compound 2 12.1 g<br>t-butyl α-trifluoromethylacrylate 7.9 g | Polymer 8 | 8.0 g | 6,400 (1.42) |
| 8 | Compound 3 1.5 g<br>t-butyl α-trifluoromethylacrylate 1.0 g | Polymer 9 | 1.2 g | 7,000 (1.36) |
| 9 | Compound 7 10.0 g<br>methyladamantylmethacrylate 6.3 g | Polymer 10 | 11.7 g | 10,200 (1.64) |
| 10 | Compound 7 10.0 g | Polymer 11 | 8.7 g | 16,500 (1.38) |
| 10 | Polymer 11 2.0 g | Polymer 12 | 1.6 g | 16,600 (1.37) |
| 11 | Compound 7 10.0 g<br>ethyladamantylmethacrylate 6.4 g<br>MA-3,5-HFA-CHOH 13.3 g | Polymer 13 | 17.2 g | 14,900 (1.55) |
| 12 | Compound 7 7.8 g<br>methyladamantylmethacrylate 4.9 g<br>MA-2-HFA-CHOH 4.7 g<br>norbornane lactone methacrylate 3.1 g | Polymer 14 | 16.6 g | 12,300 (1.51) |

Example 13

The polymer compounds 8 to 14 of Examples 7-12 were each dissolved in propylene glycol methyl acetate, and they were adjusted to a solid matter portion of 14%. Furthermore, triphenylsulfonium triflate (TPS105) made by Midori Kagaku Co., Ltd. as an acid generator was dissolved in a manner to be 2 parts by weight per 100 parts by weight of the polymer compound, thereby preparing resist solutions. These were subjected to spin coating. By a measurement of light transmittance of a film thickness of 250 nm at a wavelength of 193 nm, they were 75.0%, 74.9%, 68.8%, 74.0%, 72.5%, 73.1%, and 70.6% in the order of polymer compounds 8, 9, 10, 11, 12, 13, and 14, showing high transparency in ultraviolet region.

Then, all of the resist solutions were filtered with a membrane filer of a pore diameter of 0.2 μm. Then, each composition solution was applied to a silicon wafer by spin coating to obtain a resist film of a film thickness of 250 nm. After conducting a preliminary baking at 120° C., an exposure to a 248 nm ultraviolet ray was conducted through a photomask. Then, a post exposure baking was conducted at 120° C. Then, a development was conducted at 22° C. for 1 minute using 2.38 wt % tetramethylammonium hydroxide aqueous solution. As a result, a high-resolution pattern was obtained from each resist solution. There were almost not found inferiority defect in adhesion to substrate, film-forming inferiority defect, development defect, and etching resistance inferiority defect.

The invention claimed is:

1. A fluorine-containing cyclic compound represented by the following general formula (3):

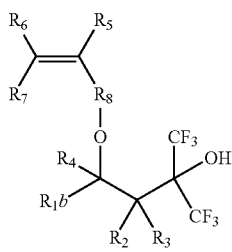

(3)

wherein

R1b is a $C_1$-$C_{25}$ cyclic alkyl group, cyclic alkenyl group, cyclic alkynyl group, aryl group, or heterocyclic group, and may contain fluorine atom, oxygen atom, sulfur atom, nitrogen atom or an atomic group containing a carbon-carbon double bond;

each of R2 to R7 is independently a hydrogen atom, a halogen atom, or a $C_1$-$C_{25}$ straight-chain, branched or cyclic alkyl group, and may contain fluorine atom, oxygen atom, sulfur atom, nitrogen atom or an atomic group containing a carbon-carbon double bond; and R8 is a carbonyl group or methylene group, or a single bond.

2. A fluorine-containing cyclic compound according to claim 1, which is represented by the following general formula (6):

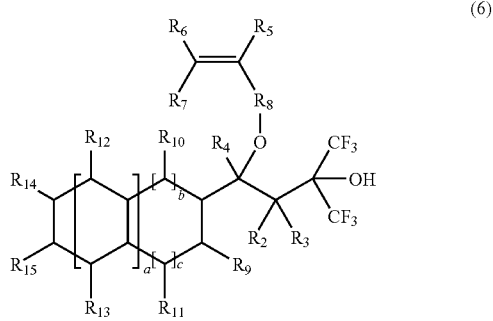

(6)

wherein each of R2 to R7 and R9 to R15 is independently a hydrogen atom, a halogen atom, or a $C_1$-$C_{25}$ straight-chain, branched or cyclic alkyl group, and may contain fluorine atom, oxygen atom, sulfur atom, or nitrogen atom;

R8 is a carbonyl group or methylene group or a single bond;

R10 and R11, R12 and R13, or R14 and R15 may be bonded together to form a ring; in such case, it is an $C_1$-$C_{25}$ alkylene group that may contain oxygen, sulfur, nitrogen or hetero atom; and "a" is 0 or 1, "b" is an integer of 0-2, and "c" is an integer of 0-2.

3. A fluorine-containing cyclic compound according to claim 1, which is represented by the following general formula (9):

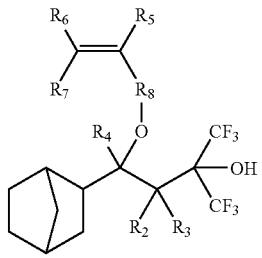

(9)

wherein
each of R2 to R7 is independently a hydrogen atom, a halogen atom, or a $C_1$-$C_{25}$ straight-chain, branched or cyclic alkyl group, and may contain fluorine atom, oxygen atom, sulfur atom, or nitrogen atom; and R8 is a carbonyl group or methylene group or a single bond.

4. A fluorine-containing polymer compound having a weight average molecular weight of 1,000 to 1,000,000, comprising a repeating unit represented by the following general formula (10):

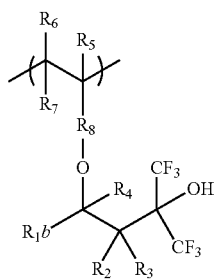

(10)

wherein
$R_1b$ represents a $C_1$-$C_{25}$ cyclic alkyl group, cyclic alkenyl group, cyclic alkynyl group, aryl group, or heterocyclic group, and may contain fluorine atom, oxygen atom, sulfur atom, nitrogen atom or an atomic group containing a carbon-carbon double bond;

each of $R_2$ to $R_7$ independently represents a hydrogen atom, a halogen atom, or a $C_1$-$C_{25}$ straight-chain, branched or cyclic alkyl group, and may contain fluorine atom, oxygen atom, sulfur atom, nitrogen atom or an atomic group containing a carbon-carbon double bond; and $R_8$ represents a carbonyl group or methylene group, or a single bond.

5. A fluorine-containing polymer compound according to claim 4, wherein the repeating unit represented by the following general formula (11):

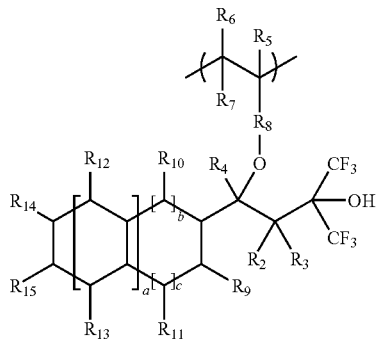

(11)

wherein
each of $R_2$ to $R_7$ and $R_9$ to $R_{15}$ independently represents a hydrogen atom, a halogen atom, or a $C_1$-$C_{25}$ straight-chain, branched or cyclic alkyl group, and may contain fluorine atom, oxygen atom, sulfur atom, or nitrogen atom;

$R_8$ represents a carbonyl group or methylene group or a single bond;

$R_{10}$ and $R_{11}$, $R_{12}$ and $R_{13}$, or $R_{14}$ and $R_{15}$ may be bonded together to form a ring: in such case, it is an $C_1$-$C_{25}$ alkylene group that may contain oxygen, sulfur, nitrogen or hetero atom; and "a" is 0 or 1, "b" is an integer of 0-2, and "c" is an integer of 0-2.

6. A fluorine-containing polymer compound according to claim 4, wherein the repeating unit is represented by the following general formula (12):

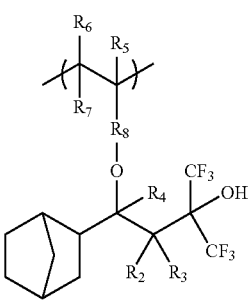

(12)

wherein
each of $R_2$ to $R_7$ independently represents a hydrogen atom, a halogen atom, or a $C_1$-$C_{25}$ straight-chain, branched or cyclic alkyl group, and may contain fluorine atom, oxygen atom, sulfur atom, or nitrogen atom; and $R_8$ represents a carbonyl; group or methylene group or a single bond.

7. A fluorine-containing polymer compound according to claim 4, which comprises a repeating unit having an acid-labile group.

8. A resist material comprising a fluorine-containing polymer compound according to claim 4.

9. A chemically-amplified resist material comprising a resist material according to claim 8 and a photoacid generator.

10. A pattern forming process comprising the steps of:
(a) applying a resist material according to claim 8 to a substrate;
(b) subjecting the substrate to a heat treatment;
(c) conducting an exposure, using a high-energy ray of a wavelength of 300 nm or less or an electron beam, through a photomask;
(d) subjecting the exposed resist film to a heat treatment; and conducting a development treatment.

11. A pattern forming process according to claim 10, wherein the high-energy ray used is $F_2$ excimer laser, ArF excimer laser, KrF excimer laser or soft X-ray.

12. A fluorine-containing polymer compound according to claim 4, wherein hydroxyl groups contained in the molecule are partially or entirely protected with protecting groups.

* * * * *